United States Patent
Hildeberg et al.

(10) Patent No.: US 8,178,746 B2
(45) Date of Patent: May 15, 2012

(54) DELIVERY DEVICE

(75) Inventors: Jenny Hildeberg, Landvetter (SE);
Anna Klinte Olsson, Askim (SE);
Ulrika Husmark, Mölnlycke (SE);
Dennis Dahl, Mölnlycke (SE)

(73) Assignee: SCA Hygiene Products AB, Göteborg (SE)

( * ) Notice: Subject to any disclaimer, the term of this patent is extended or adjusted under 35 U.S.C. 154(b) by 483 days.

(21) Appl. No.: 12/513,104

(22) PCT Filed: Nov. 2, 2006

(86) PCT No.: PCT/SE2006/001243
§ 371 (c)(1),
(2), (4) Date: Apr. 30, 2009

(87) PCT Pub. No.: WO2008/054268
PCT Pub. Date: May 8, 2008

(65) Prior Publication Data
US 2010/0262097 A1    Oct. 14, 2010

(51) Int. Cl.
*A61F 13/15* (2006.01)
(52) U.S. Cl. .................. 604/360; 604/359; 604/364
(58) Field of Classification Search ................ 604/360, 604/359, 364
See application file for complete search history.

(56) References Cited

U.S. PATENT DOCUMENTS

| | | |
|---|---|---|
| 2,066,946 A | 1/1937 | Reiman |
| 3,783,869 A | 1/1974 | Schnipper |
| 4,245,630 A | 1/1981 | Lloyd et al. |
| 4,518,696 A | 5/1985 | Gehrman et al. |
| 5,780,048 A | 7/1998 | Lee |
| 6,761,885 B1 | 7/2004 | Håkansson et al. |
| 7,523,821 B2 | 4/2009 | Assie et al. |
| 2008/0294133 A1* | 11/2008 | Gustafson et al. ............ 604/360 |

FOREIGN PATENT DOCUMENTS

| | | |
|---|---|---|
| EP | 0 122 846 A1 | 10/1984 |
| FR | 2 848 535 | 6/2004 |
| GB | 2 311 727 A | 10/1997 |

(Continued)

OTHER PUBLICATIONS

G.B. Hill et al., "Bacteriology of the Vagina," Scand. J. Urol. Nephrol., 1984, 1986 (Suppl.), pp. 23-29.

(Continued)

*Primary Examiner* — Jacqueline F. Stephens
(74) *Attorney, Agent, or Firm* — Buchanan Ingersoll & Rooney PC (57) ABSTRACT

A delivery device for a sanitary article includes an encapsulating material with a first layer and a second layer, enclosing an additive in a space formed by these layers of encapsulating material. The delivery device also includes a third layer, positioned above the second layer of encapsulating material. The third layer extends beyond and thereby covers substantially all of the edges of the second layer of encapsulating material. The third layer may also extend into and throughout the space formed between the first and second layers of encapsulating material that enclose the additive. The third layer thereby protects the user of a product comprising the delivery device from contact with the edges of the second layer of encapsulating material and also provides a means for attaching the delivery device to an article to keep it in place during transport storage and use. The invention also relates to sanitary articles, such as hygiene tissues and absorbent articles, containing the delivery device.

38 Claims, 8 Drawing Sheets

FOREIGN PATENT DOCUMENTS

| | | |
|---|---|---|
| WO | WO 92/13577 A1 | 8/1992 |
| WO | WO 93/09818 A1 | 5/1993 |
| WO | WO 95/00087 | 1/1995 |
| WO | WO 97/02846 A1 | 1/1997 |
| WO | WO 99/17813 A1 | 4/1999 |
| WO | WO 99/45099 A1 | 9/1999 |
| WO | WO 00/35502 A1 | 6/2000 |
| WO | WO 02/28446 A1 | 4/2002 |
| WO | WO 2004/060416 A1 | 7/2004 |

OTHER PUBLICATIONS

International Search Report for PCT/SE2006/001243, mailed Feb. 26, 2007.

Written Opinion for PCT/SE2006/001243, mailed Feb. 26, 2007.

Supplementary European Search Report dated Aug. 10, 2011, issued in the corresponding European Application No. 06812967.5-2124.

* cited by examiner

DELIVERY DEVICE

TECHNICAL FIELD

The present invention relates to a sanitary article, such as an absorbent article or a hygiene tissue, comprising a delivery device which comprises an additive having a beneficial effect on the skin and/or urogenital area. The invention in particular relates to sanitary articles comprising delivery devices that are convenient to use and does not cause discomfort to the user. A delivery device of an embodiment of the invention also provides means for attaching the delivery device to a sanitary article.

BACKGROUND ART

The urogenital area is a sensitive region with a delicate balance of moisture, fat and microorganisms, which is easily disturbed and which may cause discomfort and smarting. For example, the balance may be disturbed by extensive cleaning, the use of antibiotics or antifungal agents, and the use of absorbent articles that may dry out the skin and mucous membranes. It is known that the administration of different substances to the urogenital area, such as prebiotics, probiotics, skin soothing substances etc., may improve the balance in the urogenital area and/or prevent discomfort.

The urogenital area harbors a complex microbial ecosystem comprising more than 50 different bacterial species (Hill et al., Scand. J. Urol. Nephrol. 1984; 86 (suppl.) 23-29). The microbial ecosystem of a healthy individual can be disturbed by the use of antibiotics, during hormonal changes, such as during pregnancy or use of contraceptives with estrogen, during menstruation, after menopause, in people suffering from diabetes etc. Also, microorganisms may spread from the anus to the urogenital area, thereby causing infections. This results in a disturbance of the normal microbial flora and leaves the individual susceptible to microbial infections that cause vaginitis, urinary tract infections and ordinary skin infections. The dominating species in this area for fertile women are lactic acid producing bacteria. Examples of such bacteria include bacteria belonging to the genus *Lactobacillus, Lactococcus, Bacillus* and *Bifidobacteria*. These lactic acid producing members are important for retaining a healthy microbial flora in these areas, and act as probiotic bacteria with an antagonistic effect against pathogenic microbial species. Lactic acid producing bacteria inhibit growth and colonization by other microorganisms by occupying suitable niches for colonization, by forming biofilms and competing for available nutrients, thereby excluding colonization by harmful microorganisms. Also, the production of hydrogen peroxide, specific inhibiting substances, such as bacteriocines, and organic acids (including lactic acid and acetic acid) that lower the pH, inhibit colonization by other microorganisms.

Similarly to the urogenital area, the skin has a delicate balance of moisture, fat and microorganisms, which is easily disturbed by conditions that dry out the skin and that disturb the microbial balance, such as extensive cleaning.

Traditionally infections in the urogenital area and the skin caused by undesirable microbial organisms have been treated by the administration of antibacterial and antifungal agents to the affected body part. Although such agents may be used to treat infections, they may also in themselves cause a disturbed microflora.

More recently, the administration of probiotic bacteria, such as lactic acid producing bacteria, to the urogenital area and the skin has been suggested to be used in order to out-compete pathogenic species and facilitate reestablishment and maintenance of a beneficial microbial flora in these areas.

Other additives that may be used in order to improve the urogenital and skin milieu, and that therefore may be interesting to deliver to these areas, include prebiotics. Prebiotics promote a balanced microflora when administered in adequate amounts to a host. Examples are nutrition for probiotic bacteria, substances that promote adhesion to the host of probiotic bacteria and pH-regulating substances.

In addition, it may be of interest to deliver additives, such as pH regulating substances, to the skin and/or urogenital area in order to maintain and/or achieve a low pH which may be desirable. Other examples of substances that may be used to improve the milieu of skin and/or urogenital area include humidity stabilization substances, hydrophobic substances, antioxidants, skin soothing substances and odor inhibiting substances.

Additives such as cooling substances, anti-itching substances and aromatic substances may also be delivered to the skin and/or urogenital area for increased comfort.

One way to deliver these additives to the skin and/or urogenital area is to provide them via sanitary articles, such as hygiene tissues and absorbent articles. For example, it has been suggested that probiotic bacteria can be delivered via absorbent products, such as diapers, sanitary napkin, incontinence guards, panty liners and tampons, as described in, for example, WO 92/13577, WO 97/02846, WO 99/17813, WO 99/45099 and WO 00/35502. It has also been suggested to deliver probiotic bacteria via hygiene tissues, as disclosed in WO 04/060416.

However, when additives are to be delivered via sanitary articles, it is often desirable and/or necessary to enclose the additives before use of the sanitary article for different reasons.

Probiotics and odor inhibiting substances are often moisture sensitive and lose their effect when exposed to moisture. Therefore, it may be necessary to enclose such additives in moisture impervious packages during transport and storage of hygiene products comprising them.

It may also be necessary to protect the additives to be delivered from oxidation. For example, fatty acids may oxidize when in contact with air and become rancid. Other additives, such as aromatic substances and perfume, may need to be protected from evaporation. U.S. Pat. No. 2,066,946, e.g., discloses a sanitary napkin with a sealed envelope comprising an active chemical, wherein the envelope is used to keep the active chemical out of contact with the materials of the sanitary napkin and out of contact with air and vapor during storage.

It may also be desirable to have the additive to be delivered via a sanitary article in a confined area of the product in order to not spread to other parts of the product before and/or during use. When folding and packaging a sanitary article, a sticky additive, such as an additive comprising a hydrophobic substance, may stick to the package or smear over the product in an undesired manner which makes the product look messy or which may impair its function, e.g., by reducing its liquid absorbing properties. In particular, fatty acids and other hydrophobic additives may impair the liquid absorbent properties of absorbent products and therefore need to be protected from being spread over the product during transport and storage. Also, it may be of interest to deliver the additive to a specific body area of a user of the sanitary article. It may thus be preferable to have means for placing and keeping the additive in a position on the sanitary article so that this can be achieved. In addition, as the additives are to be delivered to the skin and/or urogenital area, which are sensitive areas, the means for delivery has to be comfortable to use and not causing discomfort.

Consequently, there is still a need to develop improved ways of delivering additives to the skin and/or urogenital area which protect additives from the surrounding milieu and/or keep them in a confined space, so that it is ensured that these additives are not destroyed during transport and storage and that also ensures that the properties of the sanitary article they are to be delivered via are retained. It is also of uttermost importance that the products are user friendly and comfortable to use. Also, it is desirable to provide a sanitary article wherein the delivery device is an integrated part of the sanitary article. Therefore, it is also of interest that the delivery device has means for attaching it to a sanitary article. In addition, there is still a need to develop manufacturing processes that are more efficient and less expensive.

SUMMARY OF THE INVENTION

An object of certain embodiments of the invention is to provide a sanitary article comprising a delivery device, for the delivery of additives. The delivery device is used to keep the additives in a confined space before use of the sanitary article, e.g., to protect the additives from leaking out and impairing the function of a sanitary article and/or protect the additives from the environment during transport and storage. More particularly, the object is to provide a sanitary article comprising a delivery device which is user friendly in that the delivery device does not cause any inconvenience to the user of the delivery device, and that is easier to produce. Another objective is to provide a delivery device that comprises means for attaching the delivery device to a sanitary article comprising it.

The above defined objects are achieved by certain embodiments of the present invention by providing a sanitary article, such as an absorbent article or a hygiene tissue, comprising a delivery device. The delivery device comprises a first layer and a second layer, being defined by first edges and second edges, respectively, of an encapsulating material, forming a space enclosing an additive, the first layer being placed on a user facing side of the delivery device in relation to the second layer. The delivery device also comprises a third layer positioned above the second layer of encapsulating material on a user facing side of the delivery device so that the third layer extends beyond and thereby covers substantially all of the edges of the second layer of encapsulating material. When the delivery device is to be used or is used, the first layer of encapsulating material is removed, such as by peeling the first layer off the product, or by the first layer disintegrating, e.g., when in contact with body heat or fluids, thereby exposing the additive. The second layer of encapsulating material remains in the sanitary article during use with its edges covered by the third layer on a user facing side of the delivery device.

Since the third layer of the delivery device is placed above the second layer of encapsulating material on the user facing side of the delivery device and extends over and beyond and thereby covers substantially all of the edges of the second layer of encapsulating material, the user of the delivery device is protected from exposure to these edges which otherwise, e.g., may scrape the user of the delivery device causing discomfort.

In addition, the third layer may provide means for attaching the delivery device to a sanitary article comprising it. Therefore, the delivery device may be kept in a confined space in the sanitary article comprising it and stays in place during transport, storage and use. The third layer also provides means for attaching the delivery device to a sanitary article without having to attach the delivery device in the vicinity of the enclosed additive, something which otherwise may harm the additive and requires more precision for attachment. The use of the third layer also has advantages in terms of ease and cost of production of delivery devices and sanitary articles comprising it, e.g., as the third layer may provide more than one function at the same time, the third layer, e.g., may also be the top sheet of an absorbent article.

DEFINITIONS

The term "sanitary article" refers to products that are placed against the skin of the user/wearer to absorb and contain body exudates, like urine, faeces and menstrual fluid, and also to products that are used for cleaning and caring of the skin and the urogenital area and that also can be used to deliver beneficial substances to these areas. Certain embodiments of the invention refer to disposable sanitary articles, which means articles that are not intended to be laundered or otherwise restored or reused as a sanitary article after use. Examples of disposable sanitary articles include wet wipes, dry wipes, feminine hygiene products, such as sanitary napkins, panty liners, sanitary panties, feminine inserts and tampons; diapers and pant diapers for infants and incontinent adults; incontinence pads; diaper inserts and the like.

The term "absorbent article" refers to products that are placed against the skin of the user/wearer to absorb and contain body exudates, like urine, faeces and menstrual fluid. Examples of disposable sanitary articles include feminine hygiene products, such as sanitary napkins, panty liners, sanitary panties, feminine inserts and tampons; diapers and pant diapers for infants and incontinent adults; incontinence pads; diaper inserts and the like.

By "hygiene tissue" is meant any device for wiping skin, for instance, a washcloth, patch, towelette, napkin, wet wipe, dry wipe and the like.

By "additive" is meant any substance which may be of interest to deliver to the skin and/or urogenital area of a subject, such as a human subject, including, but not limited to, substances with skin soothing properties, probiotic bacteria, cosmetic substances, odor inhibiting substances, prebiotics etc.

By "moisture-sensitive additives(s)" is meant additives that are intended to contribute to the effect and function of the product in some way and whose properties may be impaired when they are exposed to uncontrolled levels of moisture, e.g., in storage. Examples of such moisture-sensitive additives are moisture sensitive bacterial additives, such as lactobacilli, and odour-inhibiting additives, such as zeolites and silica.

Probioticum/probiotics/probiotic bacterium/probiotic bacteria in the present context relates to live microorganisms that confer a health benefit when administered in adequate amounts to a host.

Prebiotics are, in the present context, substances that promote a balanced microflora when administered in adequate amounts to a host. Examples are nutrition for probiotic bacteria, substances that promote adhesion to the host of probiotic bacteria and pH-regulating substances.

"Water activity" $a_w$ measures the vapour pressure generated by the moisture present in a hygroscopic product.

$$a_w = p/p_s, \text{ where:}$$

p: partial pressure of water vapour at the surface of the product at a specific temperature $p_s$: saturation pressure, or the partial pressure of water vapour above pure water at the same temperature as above for p. Water activity reflects the active part of moisture content or the part which, under normal circumstances, can be exchanged between the product and its environment. Water activity is usually defined under static conditions of equilibrium. Under such conditions, the partial pressure of water vapour (p) at the surface of the product is equal to the partial pressure of water-vapour in the immediate environment of the product. Any exchange of moisture between the product and its environment is driven by a difference between these two partial pressures.

By a "water-vapour impermeable" material layer is meant a material layer whose impermeability is so high that a delivery device comprised of said material layer will not allow more moisture to enter than that at which uptake the active moisture-sensitive additive present in the delivery device will essentially retain their properties. This means that the delivery device may have a highest WVTR (Water Vapour Transmission Rate) of 6 g/m²/24 h according to ASTME 398-83 at 37.8° C. (100° F.) and 90% relative humidity, preferably at most 4 g/m²/24 h, and more preferably at most 2 g/m²/24 h, even more preferably at most 1 g/m²/24 h and even more preferably at most 0.1 g/m²/24 h. The material layer used will also preferably protect the moisture-sensitive additives in such a way that said additives will retain their effect for at least 6 months, preferably for at least 9 months and most preferably for at least 12 months at 23° C. (73.4° F.) and 50% relative humidity after the packaging date.

The data and values mentioned with respect to WVTR (Water Vapour Transmission Rate) correspond to unsaturated values in accordance with the standard ASTME 398-83, which is generally applied in this field and is known to the person skilled in this art.

"Edge(s)" in the present context relates to the outer border(s) of a member, such as the second layer disclosed below.

By "top sheet" is in the present context meant the user facing layer of an absorbent article. Any additional layers placed above the top sheet of an absorbent article on a user facing side, e.g., the delivery device, are not considered as "top sheet" in the present context. However, in some preferred embodiments further discussed below, the third layer of the delivery device may also act as the top sheet of the absorbent article.

BRIEF DESCRIPTION OF THE DRAWINGS

FIG. 1 shows a side view (a) and a plan view (b) of an illustrative absorbent article.

FIG. 2 shows a side view (a) and a plan view (b) of one preferred embodiment of a delivery device of the invention.

FIG. 3 shows a side view (a) and a plan view (b) of a preferred embodiment of a delivery device of the invention, wherein the third layer is placed between a first and second layer of encapsulating material.

FIG. 4 shows a side view (a) and a plan view (b) of a preferred embodiment of a delivery device according to the present invention, wherein the third layer extends throughout the space formed between the first and second layers of encapsulating material.

FIG. 5 shows a side view (a) and a plan view (b) of a preferred embodiment of an absorbent article comprising a delivery device according to an embodiment of the present invention, wherein the delivery device is placed in an opening in the top sheet of the absorbent article, and wherein the third layer consequently constitutes the central part of the top sheet.

DETAILED DESCRIPTION OF THE INVENTION

The present invention relates to sanitary articles comprising delivery devices for delivery of additives, such as skin caring agents, odor inhibiting substances and probiotic bacteria, to the skin and/or urogenital area, which have improved user comfort and other advantages due to the design of the delivery devices, e.g., production advantages. The delivery devices are placed on sanitary articles, such as absorbent articles (e.g., sanitary napkins, panty-liners, diapers, incontinence guards, etc.) and hygiene tissues suitable for absorbing bodily fluids, or cleaning the skin, and simultaneously release an additive. Certain embodiments of the invention therefore also provides means for attaching the delivery devices to a sanitary article to keep the delivery device in place during transport, storage and use. As discussed above, such additives, for different reasons, often need to be separated from the article they are delivered via during storage and transport.

Figure 1A:
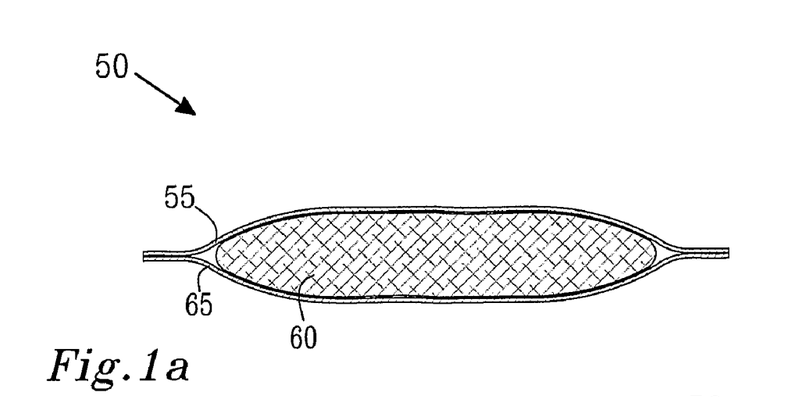
Figure 1B:
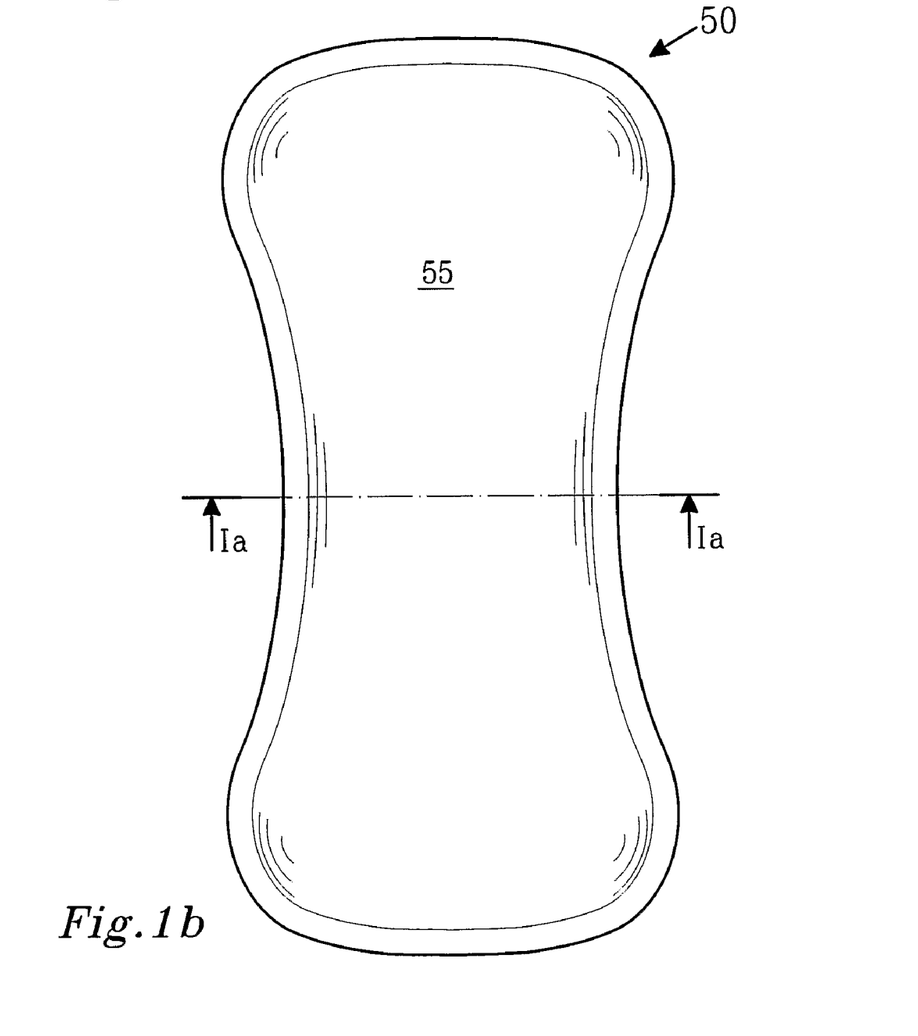

FIG. 1 discloses a schematic illustration of an absorbent article 50 comprising a top sheet 55, an absorbent structure 60 and a back sheet 65. Any additional layers placed above the top sheet 55 of the absorbent article 50 on a user facing side are not considered as "top sheet" in the present context. However, in some preferred embodiments further discussed below, the third layer of the delivery device may act as the top sheet 55 of the absorbent article 50.

FIG. 2 discloses a first embodiment of a delivery device 1 of the present invention. Also shown in FIG. 2 is an absorbent article 50 comprising the delivery device 1. Even if FIG. 2a and FIG. 2b show the delivery device 1 exemplary being placed on an absorbent article 50, the delivery device 1 in this and the following embodiments may instead be placed on any other sanitary article as defined above. Also, even if the delivery device in FIG. 2a and FIG. 2b is placed on the top sheet 55 of the absorbent article 50 on the user facing side, as the skilled person readily understands, alternative ways of placing the delivery device 1 on an absorbent article 50 are possible. Additional exemplary and non-limiting of ways of placing the delivery device 1 on an absorbent article 50 will be disclosed later.

FIG. 2 shows a delivery device 1, comprising an encapsulating material with a first layer 5 and a second layer 10, said first layer 5 being defined by first edges 45 and second layer being defined by second edges 35. The first layer 5 is placed on a user facing side of the delivery device 1 in relation to the second layer 10. Preferably, the first layer 5 and the second layer 10 are sealed together along their edges. The first layer 5 and the second layer 10 of encapsulating material may have any suitable shape, such as circular, rectangular, square shaped or irregular. The first layer 5 and second layer 10 of encapsulating material may be made of the same material or different materials. The first layer 5 and/or second layer 10 of encapsulating material are in one preferred embodiment water vapor impermeable and, in this case, more preferably both the first layer 5 and the second layer 10 of encapsulating material are water vapour impermeable.

Figure 2A:
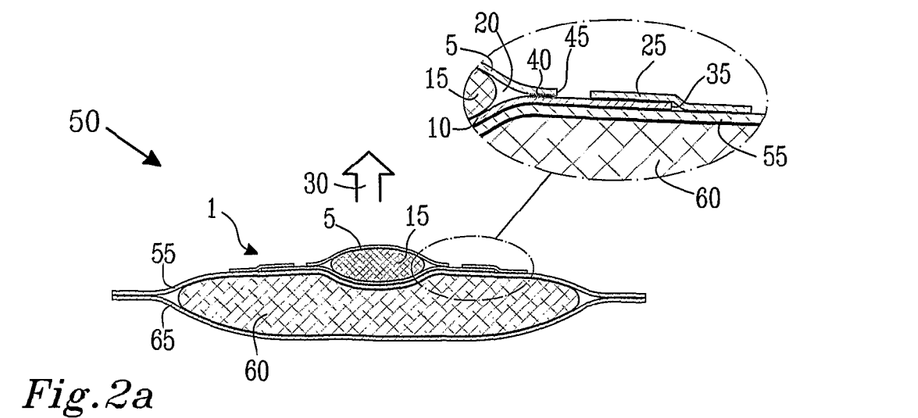
Figure 2B:
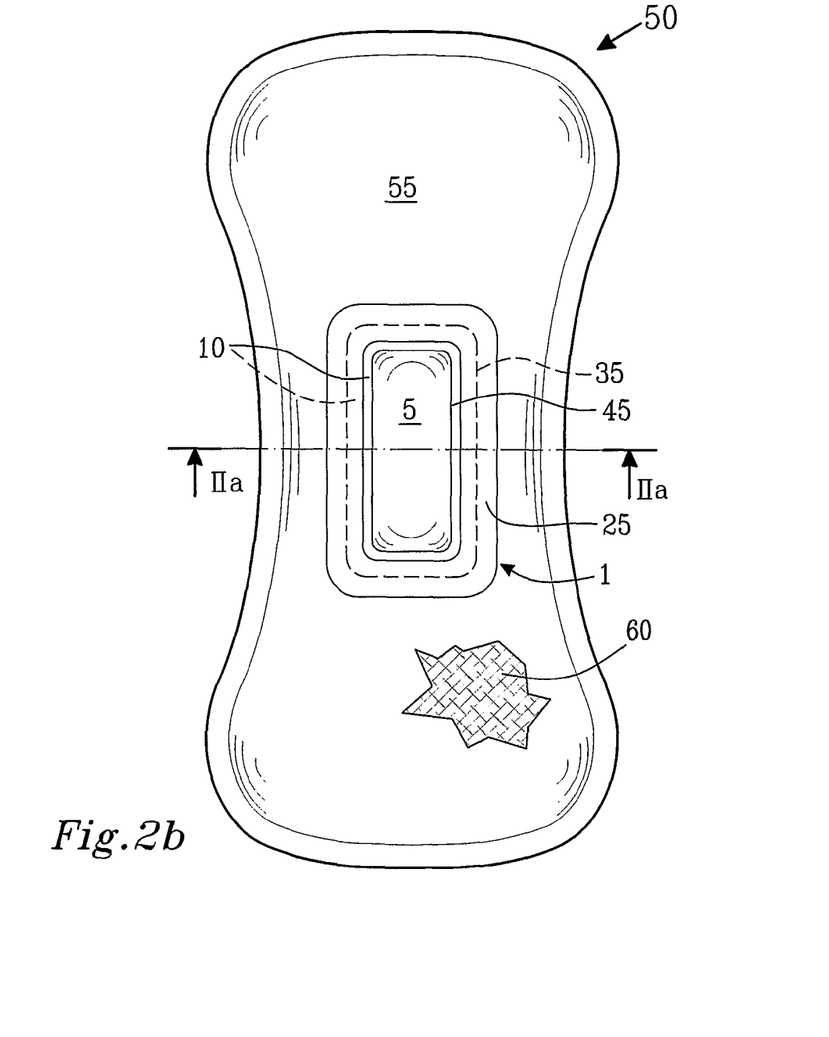

The first layer 5 and/or second layer 10 of encapsulating material may comprise a metal foil. One preferred example of such a foil is an aluminium foil. The metal foil preferably has a thickness of at least 2 μm, preferably 5-20 μm and most preferably 6-12 μm.

The first layer 5 and/or second layer 10 of encapsulating material may also comprise a polymeric film. Preferably, the polymeric film is chosen from polyethylene, polypropylene, polyesters, polyvinylchloride, polyvinyldichloride, cyclic olefinic copolymers, copolymers and mixtures thereof, metallized polyolefins and plastic laminates with ceramic barrier.

Alternatively, the first layer 5 and/or second layer 10 of encapsulating material comprise a laminate comprising a polymeric material.

The first layer 5 and/or second layer 10 of encapsulating material may also comprise a laminate of a metal foil and a polymeric material and/or wax. In a further aspect, the laminate comprises at least three laminate layers.

A laminate according to an embodiment of the invention may, for example, be a three layer laminate having a protective wear resistant layer intended to lie as an exterior protection layer, a water vapour impermeable intermediate layer and an inner sealing layer intended to face an, optionally moisture sensitive, additive. Such a laminate will preferably have a thickness of 10-400 μm, preferably 20-200 μm.

In one embodiment of the delivery device 1, the polymeric material or wax is forming the interior laminate layer facing the additive. In another embodiment, the polymeric material is forming the exterior laminate layer facing away from the additive. In yet another embodiment of a delivery device 1, both the interior laminate layer and the exterior laminate layer are formed by a polymeric material and/or a wax.

The polymeric material discussed above may preferably be produced, at least partially, from one or more polymers suitable for use in accordance with various embodiments of the invention, the polymers may be chosen from polyethylene, polypropylene, polyesters, polyethylene terephthalate, polyvinylchloride, polyvinyldichloride, cyclic olefinic copolymers, polyolefins, metallized polyolefins, ethylene vinylacetate copolymers, ethylene ethyl acrylate copolymers, ethylene butyl acrylate copolymers, polyamides, polyvinyl alcohol, starch based polymers, poly lactic acid, ionomers, copolymers, and similar polymers, and mixtures thereof.

Polymeric material with good water vapour barrier properties are polyethylene, polypropylene, polyesters, polyvinyl chloride, polyvinyl dichloride, cyclic olefinic copolymers, metallized polyolefins, and plastic laminates with ceramic barriers.

Aluminium foil, aluminium oxide or silicon oxide or the like is suitable materials for producing the encapsulating material. Other materials that may be suitable to use in the laminate in accordance with certain embodiments of the invention are plastic laminates with ceramic barriers, waxes, paper, lacquers and adhesives.

Preferred waxes for the use in laminates include plant wax, mineral wax, animal wax, silicon wax and mixtures thereof.

The first layer 5 and/or second layer 10 of encapsulating material may also comprise a metal oxide layer and/or a silicon oxide layer. More preferably, the metal oxide layer is an aluminium oxide layer.

Materials intended for forming a water-vapour impermeable first layer 5 and second layer 10 of encapsulating material are often expensive and preferably the thinnest possible material layer is used while the required strength properties are still maintained. In order to produce an encapsulating material that has good wear strength and can be readily sealed, a less expensive material may be used as outer protective wear resistant layer and/or as inner sealing layer (as defined above). For instance, the encapsulating material includes an inner laminate layer that enables a good sealing between the first layer 5 and second layer 10 of encapsulating material to be obtained, e.g., polyolefins, e.g., polyethylene and polypropylene, polyamides, ionomers or waxes, an intermediate laminate layer that consists of a material having good water-vapour impermeability to be chosen from the materials aluminium, aluminium oxide, silicon oxide, polyethylene, polypropylene, polyesters, polyvinylchloride, polyvinyldichloride, cyclic olefinic copolymers, polyolefins, metallized polyolefins, polyamide (nylon) or plastic laminates with ceramic barrier and a wear resistant outer layer, e.g., polyesters, polyethylene or polypropylene. The encapsulating material may consist of one to ten laminate layers of different materials. Non-limiting examples of laminates are high barrier aluminium laminates and high barrier aluminium-free laminates, CERAMIS®—both from ALCAN Packaging Cramlington Ltd.

When the first layer 5 (and/or, in particular cases as later discussed, second layer 10) of encapsulating material is to be removed by disintegration of the layer, as discussed later, suitable materials for the first layer 5 (and/or second layer 10) include water soluble films, such as polyvinyl alcohol, poly lactic acid and starch-based films, and fat soluble films.

The first layer 5 and the second layer 10 of encapsulating material enclose an additive 15 in a space 20 formed between the first layer 5 and the second layer 10 of encapsulating material. Since the first layer 5 and second layer 10 enclose the additive 15, the additive 15 stays in place in the delivery device 1 before use. Also, the additive 15 is protected from influence of the surrounding environment, such as exposure to moisture or dry conditions, which may destroy the additive 15 before use of the delivery device 1. Different types of additives 15 may need protection from different environmental influences. Depending on the specific additive 15, different choices of material of the first layer 5 and second layer 10 of encapsulating material may be suitable. For example, moisture sensitive additives, such as probiotics or an odor inhibiting substance, may need protection from moisture; a hydrophobic substance, such as an oil, may need protection from oxidation; aromatic substances and perfume may need protection from evaporation; and light sensitive additives may need protection from light. In addition, as previously mentioned, additives comprising hydrophobic substances may impair the liquid absorbent properties of sanitary articles and therefore need to be protected from being spread over the product during transport and storage. The above described objective of providing protection for the additive may be achieved by the delivery device 1 in various embodiments of the invention.

The additive 15 to be delivered by the delivery device 1 may comprise any substance for improved health and hygiene desirable to transfer to a subject, such as a substance having a beneficial effect on the skin and/or urogenital area or a substance that improves the appearance of the skin and/or urogenital area. One preferred example of an additive 15 comprises skin caring agents, such as lotions and oils. Another preferred example includes prebiotics, i.e., substances that promote a balanced micro flora when administered in adequate amounts to a host. Examples of prebiotics are nutrition for probiotic bacteria, substances that promote adhesion to the host for probiotic bacteria, pH-regulating substances. Other examples of preferred additives include pH regulation substances, such as buffered citric acid, humidity stabilisation substances, such as Carbamide, botanical substances, such as Aloe Vera, antioxidants, such as ascorbic acid, vitamins, skin soothing substances, and hydrophobic substances, such as olive oil. It may also be preferred to use antibacterial substances, such as ZnO, and antifungal substances as additives in order to combat microbial infections. Examples of preferred additives also include additives for comfort and pleasure, such as cooling substances, anti itching substances and aromatic substances.

In another preferred example, the additive 15 comprises an odor inhibiting substance. Examples of preferred odor inhibiting substances are zeolites and silica.

In one preferred embodiment, the additive 15 in the delivery device 1 comprises probiotic bacteria. Preferably such probiotic bacteria are lactic acid producing bacteria, e.g., from the genera *Lactobacillus, Lactococcus* and *Pediococcus*. More preferably the lactic acid producing bacteria are from the genera *Lactobacillus*, such as *Lactococcus lactis, Lactobacillus rhamnosus, Lactobacillus fermentum, Lactobacillus acidophilus, Lactobacillus curvatus* or *Lactobacillus plantarum*. In one preferred embodiment of the present invention, the delivery device comprises *Lactobacillus plantarum* 931 (deposited at Deutsche Sammlung von Mikroorganismen und Zellkulturen GmbH and assigned accession number DSM 11918, see e.g. EP 1060240), that has been shown to being able to be transferred to and survive in the urogenital area. In addition, *Lactobacillus plantarum* 931 has been shown to be able to inhibit the growth of other microorganisms, thereby showing valuable properties as a probiotic bacterium.

The probiotic bacteria may preferably be dried bacteria, such as freeze dried, spray dried or air dried bacteria.

The delivery device 1 preferably comprises $10^4$ to $10^{11}$ colony forming units (cfu), more preferably $10^6$ to $10^{10}$ cfu, even more preferably $10^8$ to $10^{10}$ CFU, of probiotic bacteria per delivery device 1.

The additive 15 of the delivery device 1 may also preferably comprise one or more pharmaceutically acceptable carriers, excipients and/or diluents. Generally such agents should be non-toxic to the recipients at the concentrations and dosages used. Examples of such agents are buffers, thickening agents of gel forming agents, such as glycerine, polyethylene glycol, antioxidants (e.g., ascorbic acid), polypeptides of low molecular weight (less than about 10 residues), proteins, carbohydrates including glucose, sucrose and dextrins. Examples of pharmaceutical carriers include sugars, such as lactose, glucose, sucrose and trehalose; starches, such as corn starch and potato starch; cellulose and its derivatives such as sodium carboxymethylcellulose, ethylcellulose and cellulose acetates; powdered traganth, malt; gelatin; pectin; talc; stearic acids; magnesium stearate; calcium sulfate; polyols such as propylene glycol, glycerine, sorbitol, manitol, and polyethylene glycol; agar; alginic acids; pyrogen-free water; isotonic saline; and phosphate buffer solution.

Examples of preferred pharmaceutically acceptable carriers for probiotic bacteria are sugars and native starch. In addition, nutrients for bacterial propagation, such as amino acids, peptides, nucleic acid derivatives, vitamins, fatty acids, glucose, fructose, ribose, maltose and lactose may be present in the additive 15, alone or in different combinations.

Probiotic bacteria may also preferably be mixed with a carrier that enhances transfer of the bacteria to the user of the delivery device 1. Examples of such carriers include sticky agents, such as petrolatum, an oil, or a wax. Such carriers may also preferably be included in delivery devices 1 comprising additives not comprising probiotic bacteria.

Preferably, a hydrophobic carrier providing an anhydrous environment may also be used as a carrier for, e.g., moisture sensitive additives, such as probiotic bacteria. Such an anhydrous environment prolongs the survival of the bacteria during manufacture, transport and storage (see e.g. U.S. Pat. No. 4,518,696; WO 92/13577; WO 02/28446).

One example of hydrophobic carriers is lipid carriers including petroleum-derived lipids, such as paraffinum liquidum (mineral oils, paraffin oils, and Vaseline oils), petrolatum (Vaseline and petroleum jelly), cera microcrystalline, ozokerite, ceresine and paraffins. Alternatively, synthetic lipids, such as dimethicone, cyclomethicone and silicone esters can be used. A third alternative is to use plant-derived lipids, which usually are triglycerides. The plant-derived lipids are often mixtures of mono-, di- and triglycerides and free fatty acids. The lipids may be purified, hydrogenated, refined, modified and used alone or in different mixtures.

As lipid carriers often are "sticky" the use of lipid carriers has the additional advantage of increasing the transfer of the additive to the user (as discussed above). Preferred examples of lipid carriers include mineral oil based lipids, such as petrolatum.

The additive 15 of the delivery device 1 of an embodiment of the invention may also comprise wetting agents and lubricants, such as sodium lauryl sulfate, and coloring agents, lubricants, such as carbamide, stabilizers and preservatives.

A delivery device 1 according to an embodiment of the present invention may comprise one type of additive or a combination of additives, such as probiotic bacteria and odor inhibiting substances in the same delivery device 1.

In one embodiment, the additive, optionally with one or more pharmaceutically acceptable carriers, excipients and/or diluents, is placed in or on a material, such as a non-woven fabric or the materials discussed below to be suitable for the third layer, which then is placed in the space formed by the first layer 5 and second layer 10 of encapsulating material. This additional material then acts as a carrier for the additive. The use of this type of carrier may, e.g., be preferred when the additive is of low viscosity.

The delivery device 1 in addition comprises a third layer 25 positioned above the second layer 10 of encapsulating material on a user facing side 30 (indicated by an arrow 30 pointing in the direction of the user) of the delivery device 1. The third layer 25 is placed above the second layer 10 of encapsulating material so that it extends beyond the edges 35 of the encapsulating layer, both in the direction pointing towards the delivery device and in the direction pointing away from the delivery device, in order to thereby cover substantially all of the edges 35 of the second layer 10 of encapsulating material on a user facing side 30 of the delivery device 1. The size, shape and material of the third layer 25 is not critical as long as it extends beyond and thereby covers substantially all of the edges 35 of the second layer 10 of encapsulating material on the side of it that faces the user 30. Preferably at least 70%, more preferably 80%, even more preferably 90%, most preferably 100% of the edges are covered by the third layer 25. Preferably, the third layer extends at least 1.5 mm, more preferably at least 5 mm, and most preferably at least 10 mm outside of the edges 35 of the second layer 10 of encapsulating material, in the direction pointing away from the delivery device 1.5 mm is desirable to provide protection from scraping of the second layer 10 of encapsulating material when the delivery device 1 is used. If the third layer 25 extends at least 10 mm, this provides the possibility of attaching the delivery device 1 to a sanitary article via the third layer 25. Finally, if the third layer 25 extends at least 25 mm outside the edges 35 of the second layer 10 of encapsulating material, this extension is sufficient to avoid the additive being affected by the attachment method when the delivery device 1 is attached to a sanitary article via the third layer 25, as later discussed.

Preferably, in the direction pointing towards the delivery device 1, the third layer 25 extends at least 1.5 mm in order to protect the user from scraping of the second layer 10 and more preferably at least 2 mm in order to also provide means for attaching the third layer 25 to the second layer 10.

The third layer 25 may preferably comprise a porous/perforated material. Examples of preferred porous materials include non-woven, wadding or filter foam. Alternatively, preferably the third layer 25 comprises a plastic film, such as a polyethylene film, polypropylene film and/or a mixture and/or laminate of a polyethylene film and a polypropylene. The plastic film may preferably be perforated or porous.

Figure 2C:
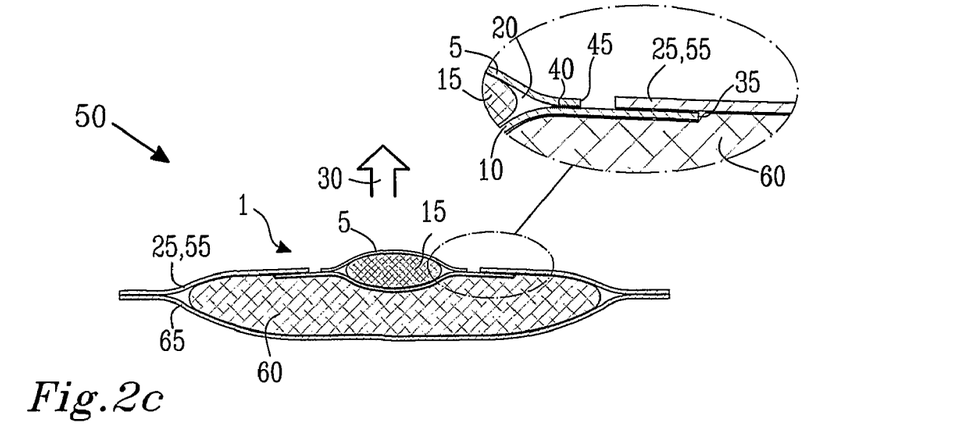
FIGS. 2c-d show a variant of this embodiment wherein the third layer also is the top sheet of an absorbent article.
Figure 2D:
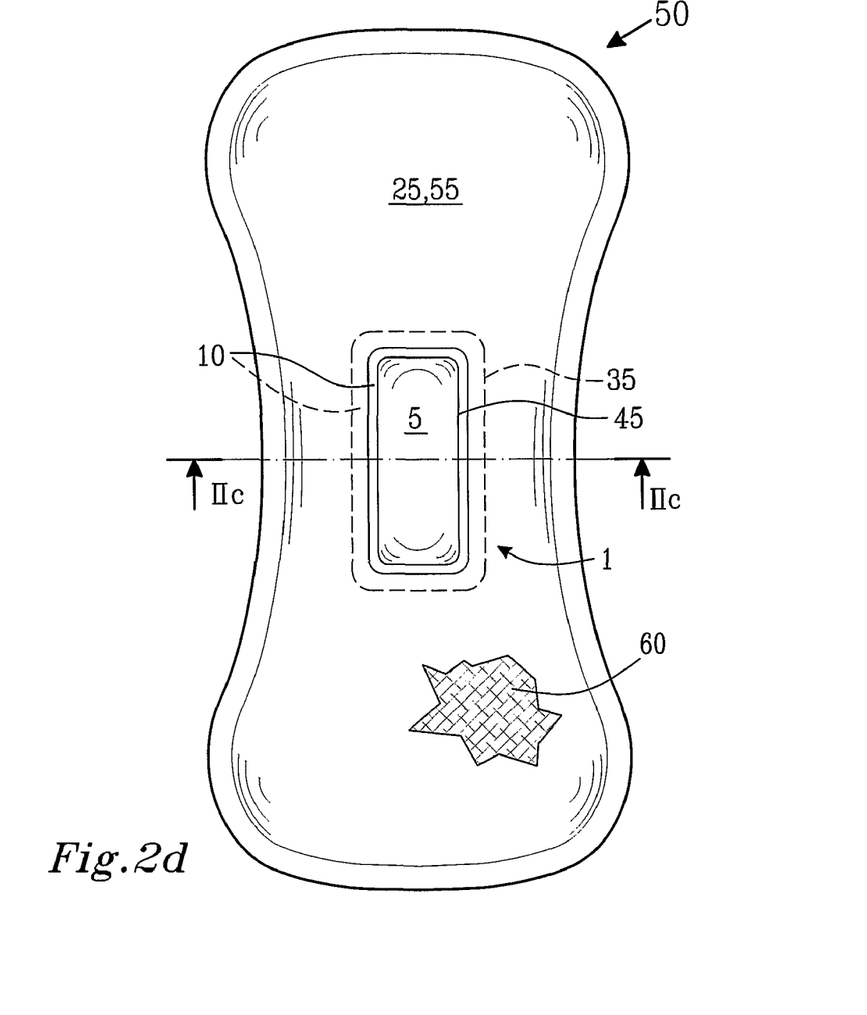

In one preferred variant of this embodiment, illustrated in FIG. 2c-d, in an absorbent article 50 comprising the delivery device 1, the third layer 25 replaces the top sheet 55, thereby acting both as the top sheet 55 and the third layer 25.

When the delivery device 1 is to be used or is used, the first layer 5 of encapsulating material is removed, thereby exposing the additive 15. The first layer 5 of encapsulating material may be removed, e.g., by peeling or tearing the first layer 5 off the delivery device 1. Alternatively, the first layer 5 may comprise a material that is dissolved by body heat or bodily fluids and thereby disintegrates when the delivery device 1 is used. In the present context "remove" means both an actual removal of the first layer 10 of encapsulating material and a disintegration of the encapsulating material.

The use of a third layer 25 in a delivery device 1 has several advantages. Since the third layer 25 is placed above the second layer 10 of encapsulating material so that it extends beyond and thereby covers substantially all of the edges 35 of the second layer 10 of encapsulating material on the user facing side 30 of the delivery device 1, the user of the delivery device 1 is protected from exposure to the edges 35 of the second layer 10 of encapsulating material when the delivery device is used. This feature is present in all the following embodiments. In this way, the edges 35 of the second layer 10 of encapsulating material that otherwise may harm and cause discomfort and inconvenience to a user of a delivery device 1, are hidden away from the user.

In addition, the third layer 25 in all embodiments may provide means for attaching the delivery device 1 to a sanitary article comprising the delivery device 1. The third layer 25 may preferably be attached, e.g., by ultrasonic welding, gluing, sewing or heat and/or cold sealing, to a sanitary article. In this case, preferably the second layer 10 of encapsulating material is attached to the third layer.

The third layer 25 also provides the possibility of attaching the delivery device 1 to a sanitary article without having to attach the delivery device 1 via the first layer 5 and/or second layer 10 of encapsulating material enclosing the additive 15. Thereby, the additive 15 is less exposed to the negative impact that the method for attaching the delivery device to a sanitary article, e.g., ultrasonic welding or heat sealing, may have on the additive 15. Also, the third layer 25 increases the area of the delivery device 1 so that less precision is required when attaching the delivery device to a sanitary article and the third layer 25 thereby facilitates the process of attaching the delivery device 1 to a sanitary article comprising it.

By attaching the delivery device 1 to the article comprising it, the risk that the whole delivery device 1 is detached from the article when the first layer 5 of encapsulating material is removed, or reduced, as the delivery device is attached to the product via the third layer 25 and not via the encapsulating material itself.

Attachment of the delivery device 1 to a sanitary article comprising it, may also ensure that the additive is positioned on the article so that it comes in contact with the preferred area of the body of the user of the sanitary article. For example, if one wants to deliver an additive to the vaginal area via an absorbent article, the delivery device 1 is attached via the third layer 25 in the absorbent article on the part of the absorbent article 50 that will come in contact with the vaginal area of the user when in use. The delivery device 1 then stays in this position both during transport, storage and during use.

The third layer 25 may preferably be attached to the second layer 10 of encapsulating material on the user facing side 30 of the second layer 10 of encapsulating material, e.g., by ultrasonic welding, heat sealing, heat sealing at low temperatures, cold sealing or by gluing.

Preferably, the first layer 5 and second layer 10 of encapsulating material are sealed together along their edges by a sealing 40 to form the space 20 enclosing the additive 15. Importantly, if the first layer 5 is not made of a material that disintegrates when the delivery device 1 is used, the sealing 40 has to be designed so that it is possible to peel off the first layer 5 of encapsulating material. Suitable sealing methods are, e.g., ultrasonic welding, heat sealing, heat sealing at low temperatures, or cold sealing. In the case of cold sealing and heat sealing at low temperatures, a sealing layer, such as, e.g., polyethylene ethyl acrylate, polyethylene vinyl acetate or wax, may be applied to the sealing side of the encapsulating material. This sealing layer can be applied over the whole of the surface or solely where sealing shall occur, so-called border coating.

The first layer 5 and second layer 10 of encapsulating material may also be glued together to form said sealing 40.

When the additive 15 enclosed in the space 20 formed by the first layer 5 and second layer 10 of encapsulating material, is moisture sensitive, in order to ensure the prevention of the ingress of moisture into the space 20, it is desirable that the first layer 5 and second layer 10 of encapsulating material are completely closed with tight sealings so that the WVTR will be at most 6 $g/m^2/24$ h measured in accordance with ASTME 398-83 at 37.8° C. (100° F.) and 90% relative humidity, preferably at most 4 $g/m^2/24$ h, and more preferably at most 2 $g/m^2/24$ h, even more preferably at most 1 $g/m^2/24$ h, and even more preferably at most 0.1 $g/m^2/24$ h, even when measured across the sealing between the first layer 5 and second layer 10 of encapsulating material, optionally holding the third layer in between.

The width of the sealing 40 between the first layer 5 and second layer 10 of encapsulating material and the choice of material of the first layer 5 and second layer 10 will influence the time it takes for the water-vapour to diffuse into space between these layers. The width of the sealing necessary for obtaining the above desirable WVTR will therefore vary. The skilled person knows how to measure the WVTR for a specific encapsulating material and a specific sealing. The skilled person can therefore determine the necessary width of the sealing 40 in order to obtain the desired WVTR. A specific width of the sealing may also be necessary to protect volatile additives, such as perfume, or additives that are sensitive to drying out, from being destroyed during transport and storage. For additives 15 that are not moisture sensitive or otherwise require protection from the surrounding environment during transport and storage, the width of the sealing is not critical.

In some embodiments, the size of the first layer 5 and second layer 10 of encapsulating material may have a length of 1-20 cm, preferably 2-15 cm, most preferably 3-10 cm and a width of 0.5-10 cm, preferably 1-8 cm, most preferably 2-5 cm. The width and/or length of the first layer 5 and second layer 10 of encapsulating material may vary along their lengths and/or widths, respectively. The size and shape of the third layer 25 can be chosen so that the third layer 25 extends beyond and thereby covers substantially all of the edges 35 of the second layer 10 of encapsulating material, as previously discussed, in order to provide protection from the edges 35 of the second layer 10 of encapsulating material and to provide a means for attaching the delivery device 1 to an article comprising it.

FIG. 3 shows an alternative embodiment of a delivery device 1, placed on a sanitary article exemplified by an absorbent article 50, as previously discussed.

Figure 3A:
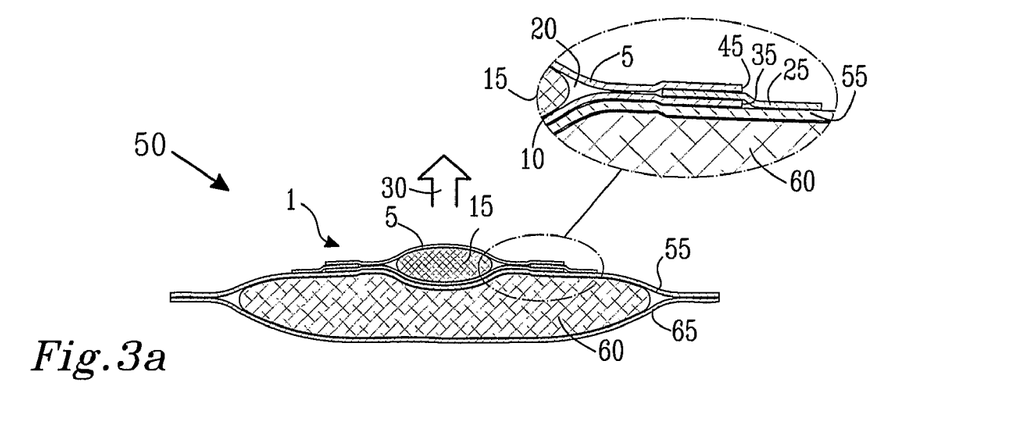
Figure 3B:
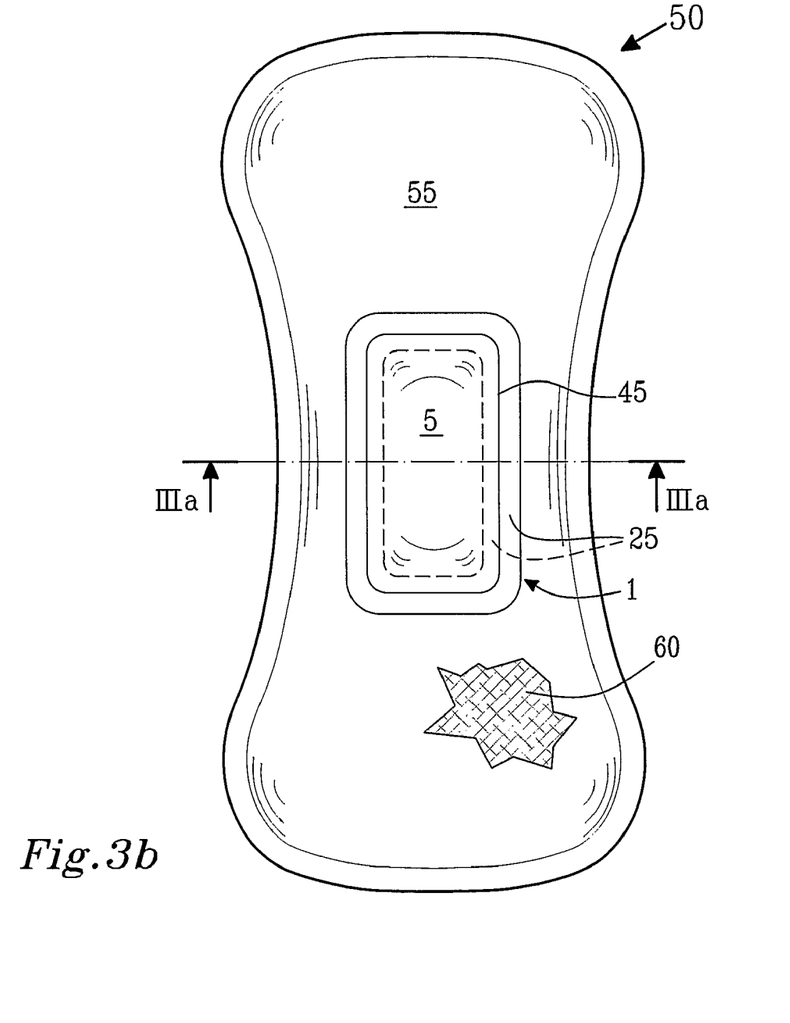

In this embodiment, the third layer 25 is instead placed between the first layer 5 and second layer 10 of encapsulating material. The third layer 25 also in this embodiment is of a size and placed so that it extends beyond and thereby covers substantially all of the edges 35 of the second layer 10 of encapsulating material on the user facing side 30 of the delivery device 1. Thereby, also in this embodiment, the user of the delivery device is protected from exposure to the edges 35 of the second layer 10 of encapsulating material and the third layer 25 provides a means for attaching the delivery device 1 to an article comprising it. The position of the edges 45 of the first layer 5 of encapsulating material in relation to the edges 35 of the second layer 10 of encapsulating material is not critical, as long as it is possible to place the third layer 25 in any extent between them. Optionally, the third layer 25 may or may not further extend in any extent into the space 20 formed between the first layer 5 and the second layer 10 of encapsulating material. Preferably, the third layer 25 is attached to at least the second layer 10 of encapsulating material. More preferably, the third layer 25 is sealed together with the first layer 5 and second layer 10 of encapsulating material in between these two layers, e.g., by ultrasonic welding, heat sealing, heat sealing at low temperatures, cold sealing or by gluing.

Figure 3C:
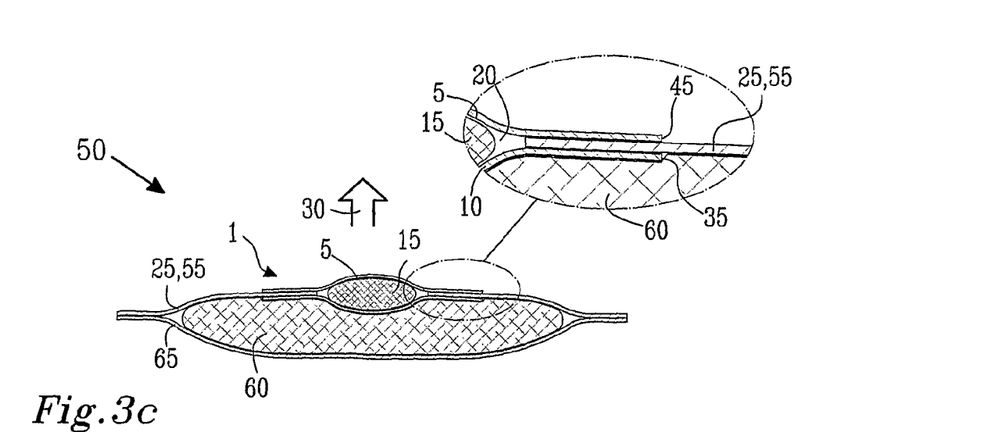
FIGS. 3c-d show a variant of this embodiment wherein the third layer also is the top sheet of an absorbent article.
Figure 3D:
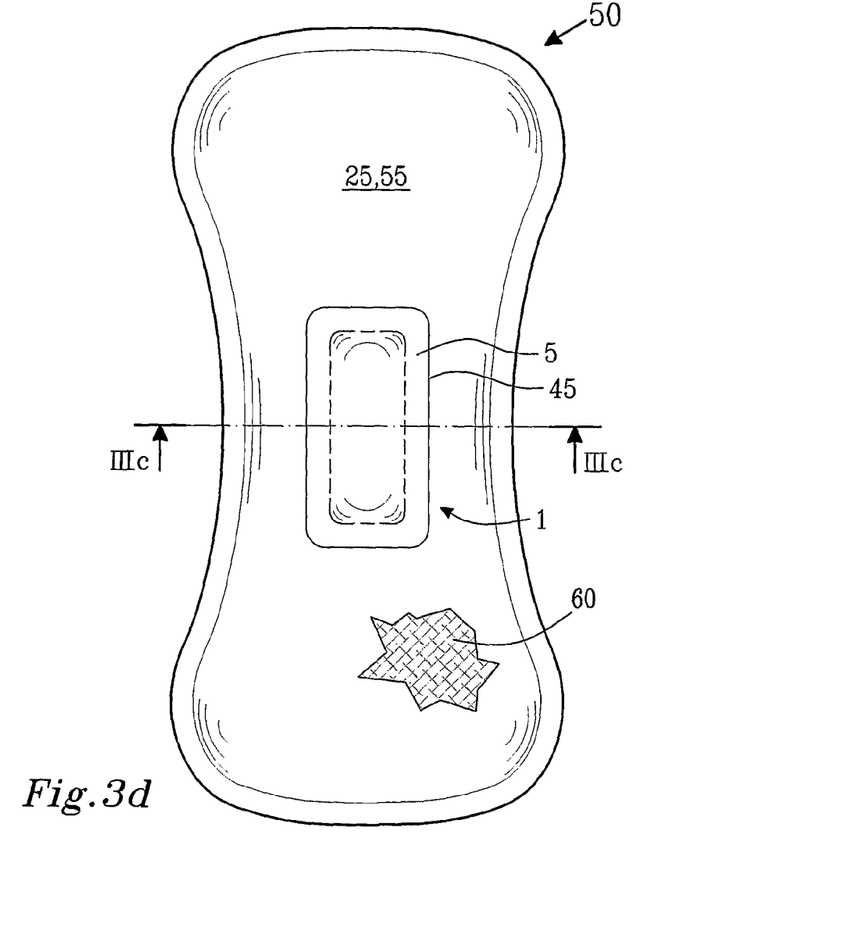

Also in this embodiment, in a preferred variant, in an absorbent article 50 comprising the delivery device 1, the third layer 25 may replace the top sheet 55, i.e. the third layer 25 also becomes the top sheet 55 of the absorbent article 50, as illustrated in FIG. 3c-d.

FIG. 4 shows another alternative, preferred embodiment of a delivery device 1, placed on a sanitary article exemplified by an absorbent article 50, as previously discussed.

Figure 4A:
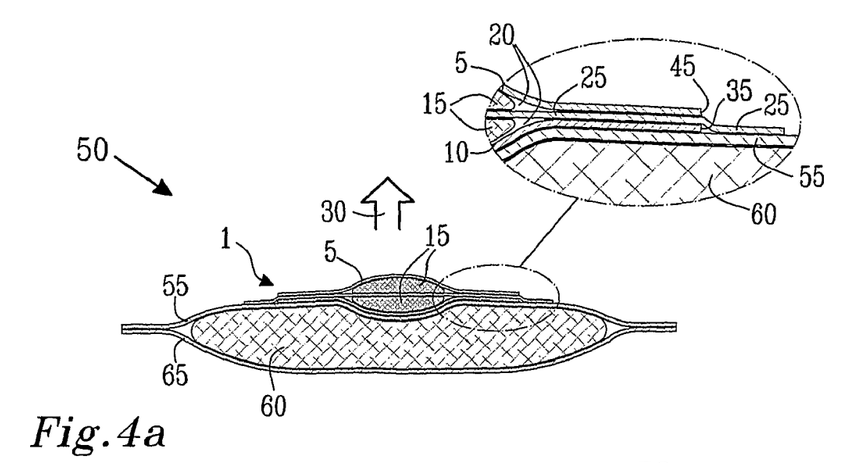
Figure 4B:
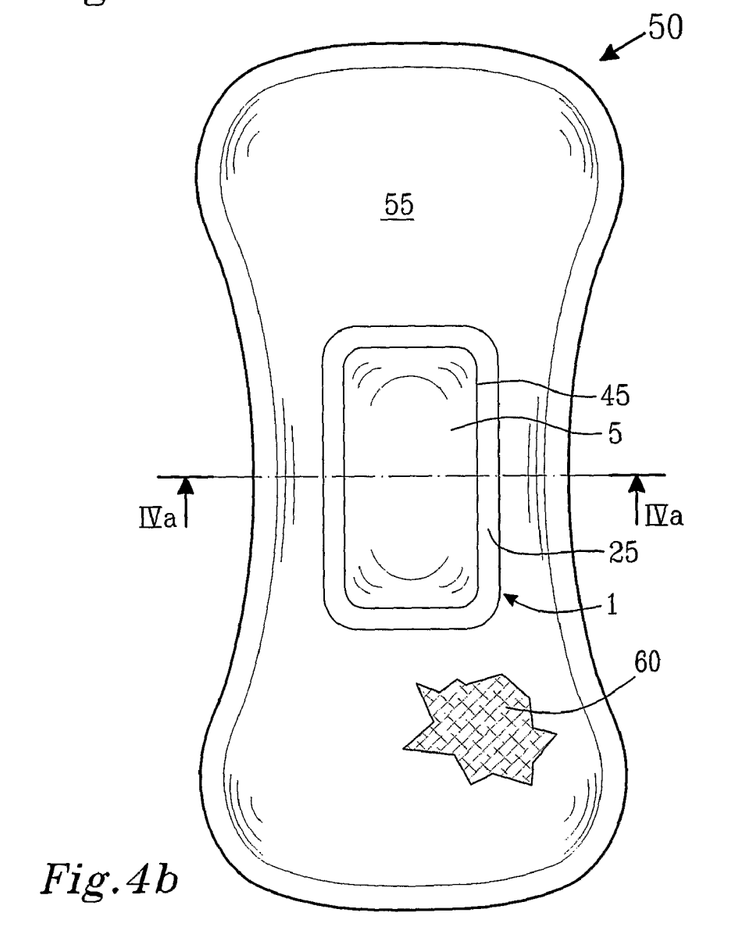

In this embodiment, the third layer 25 instead is placed between the first layer 5 and the second layer 10 of encapsulating material and extends substantially throughout the delivery device 1. Preferably, the first layer 5 and/or second layer 10 of encapsulating material are sealed together with the third layer 25 in between. Preferably, the third layer 25 extends fully throughout the space 20 formed between the first layer 5 and second layer 10 of encapsulating material. However, the third layer 25, if preferred, may have e.g. holes, incisions or slits in it, symmetrically or asymmetrically positioned over the third layer 25, even in the part that is inside the space 20 formed between the first layer 5 and second layer 10 of encapsulating material.

In FIG. 4, the third layer 25 is placed in the middle of the space 20 formed between the first layer 5 and second layer 10 of encapsulating material, when viewed from the side (FIGS. 4a and c). However, in any embodiment where the third layer 25 extends into or throughout the space 20 formed between the first layer 5 and second layer 10 of encapsulating material, the third layer 25 can be positioned anywhere in this space, such as intermediate between the first layer 5 and second layer 10 of encapsulating material, or close to or attached to (e.g. by ultrasonic welding, heat sealing, heat sealing at low temperatures, cold sealing or by gluing) the first layer 5 or second layer 10 of encapsulating material. In addition, the additive 15 may be placed anywhere in this space, such as on, above or below the third layer 25.

In one preferred embodiment, the additive 15 is placed below the third layer 25, i.e. between the third layer 25 and the second layer 10 of encapsulating material. This embodiment has several additional advantages. In this embodiment, the risk that the additive 15 is removed from the delivery device 1, e.g., by being washed away by bodily fluids or being rubbed off the delivery device 1 during use, is reduced. Also, one avoids that the additive sticks to the first layer 5 of encapsulating material and is removed with the first layer 5, when this is removed before use of a sanitary article comprising the delivery device 1. This embodiment also provides a possibility of controlling the release of the additive 15, e.g., by having an additive that is dissolved and transferred to the user first at the time of urination, or an additive that is dissolved by body heat, as the additive is separated via the third layer 25 from the user until said events occur. Consequently, in this way, one may control that the additive 15 is not transferred to the user of the delivery device 1 until one wants to. In this embodiment, it is important that the third layer 25 comprises a material that allows the additive 15 to be transferred through it, such as a perforated or porous material.

Also in this embodiment, the third layer 25 is of a size and placed so that it extends beyond and thereby covers substantially all of the edges 35 of the second layer 10 of encapsulating material on the user facing side 30 of the delivery device 1, as previously discussed. Preferably, the third layer 25 is attached to the second layer 10 of encapsulating material. More preferably, the first layer 5 and second layer 10 of encapsulating material are sealed together with the third layer 25 in between.

In all embodiments wherein the third layer 25 extends partly or fully into the space 20, formed between the first layer 5 and second layer 10 of encapsulating material, the third layer 25 has the additional advantage of being able to act as a carrier for the additive 15. The additive 15 may be impregnated, dried in, powdered, or in any other way placed on, above or below the third layer 25 in the space 20 enclosed by the first layer 5 and second layer 10 of encapsulating material. One advantage with this is that the additive 15 may be incorporated into the third layer 25 at the time of production of third layer material.

Figure 4C:
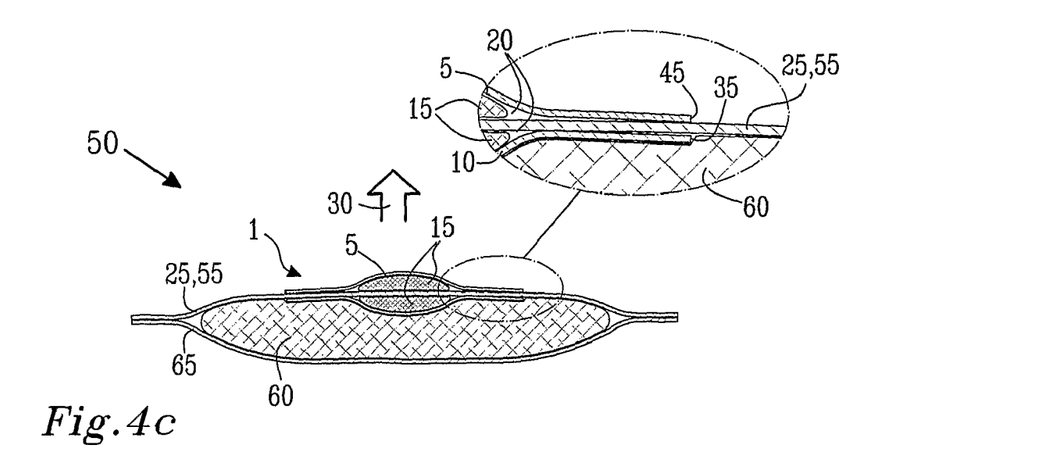
FIGS. 4c-d show a variant of this embodiment wherein the third layer also is the top sheet of an absorbent article.
Figure 4D:
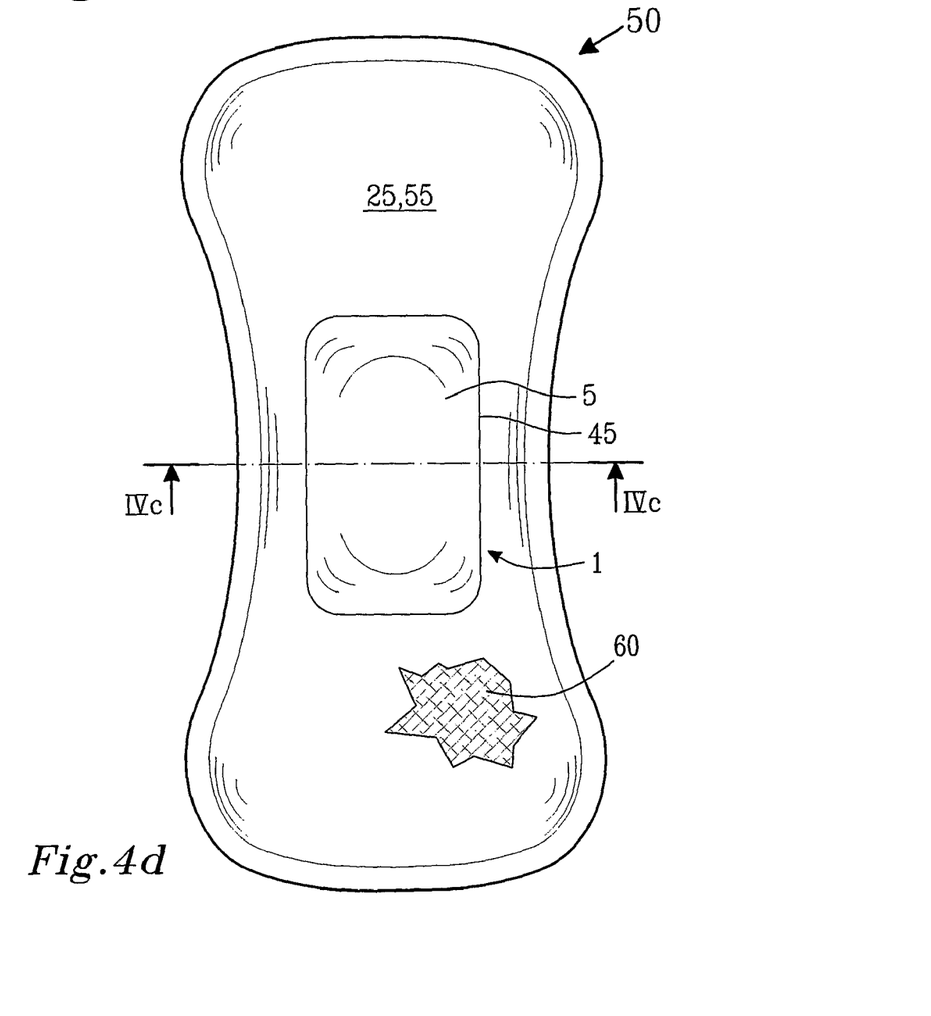

Also in this embodiment, in an absorbent article 50 comprising the delivery device 1, the third layer 25 may replace the top sheet 55, i.e., the third layer 25 also becomes the top sheet 55 of the absorbent article 50, as illustrated in FIGS. 4c-d.

The delivery device 1 of an embodiment of the present invention is placed on/in a sanitary article, such as a wet wipe, dry wipe, feminine hygiene product, such as a sanitary napkin, panty liner, sanitary panty or tampon; a diaper or pant diaper for infants and incontinent adults; incontinence pad; diaper insert and the like, as previously defined.

In one preferred embodiment, the delivery device 1 is comprised in a hygiene tissue, such as a wet wipe or a dry wipe. The use of a hygiene tissue to deliver an additive is advantageous as there is a good transfer of the additive to the user as the hygiene tissue is brought into close contact with the user when used. By placing a delivery device 1 on a hygiene tissue for the delivery of an additive, one avoids the additive being spread over the whole hygiene tissue. The user of the hygiene tissue may therefore avoid having to touch the additive with his or her hands when using the hygiene tissue. It may, e.g., be undesirable having to touch a sticky additive with one's hands when using a hygiene tissue comprising such an additive.

Also, as the delivery device comprises a second layer 10 of encapsulating material, this prevents the additive from spreading through the product, again leading to a less messy product which is easier to use and that looks more appealing.

In another preferred embodiment, the delivery device 1 is placed in/on an absorbent article 50. An absorbent article 50 according to an embodiment of the present invention typically comprises a liquid permeable topsheet, facing the user, a liquid impermeable backsheet on the side of the article facing away from the user and an absorbent structure enclosed there between. The liquid permeable topsheet can be composed of a nonwoven material, e.g. spunbonded, meltblown, carded, hydroentangled, wetlaid etc. Suitable nonwoven materials can be composed of natural fibers, such as woodpulp or cotton fibres, manmade fibres, such as polyester, polyethylene, polypropylene, viscose etc. or from a mixture of natural and manmade fibres. The topsheet material may further be composed of tow fibres, which may be bonded to each other in a bonding pattern, as, e.g., disclosed in EP-A-1 035 818. Further examples of topsheet materials are porous foams, apertured plastic films, laminate of nonwoven, perforated plastic films etc. The materials suitable as topsheet materials should be soft and non-irritating to the skin and be readily penetrated by body fluid, such as urine or menstrual fluid.

The liquid impermeable backsheet may consist of a thin plastic film, e.g., a polyethylene or polypropylene film, a nonwoven material coated with a liquid impervious material, a hydrophobic nonwoven material, which resists liquid penetration. Laminates of plastic films and nonwoven materials may also be used. The backsheet material is preferably breathable so as to allow vapour to escape from the absorbent structure, while still preventing liquids from passing through the backsheet material.

The topsheet and the backsheet have a somewhat greater extension in the plane than the absorbent structure and extend outside the edges thereof to form projecting portions. The top layer and back sheet are connected to each other within the projecting portions, e.g., by gluing or welding by heat or ultrasonic. The topsheet and/or the backsheet may further be attached to the absorbent structure by any method known in the art, such as adhesive or welding by heat or ultrasonic etc. The absorbent structure may also be unattached to the topsheet and/or the backsheet.

Fastening means in the form of an adhesive is provided on the side of the backsheet facing away from the user during use. The adhesive may releasably attach to the undergarment of the user. A release paper may protect the adhesive region before use. The adhesive region may have any suitable configuration, such as elongate or transverse strips, dots, full-coated areas etc.

In other embodiments of absorbent articles, other types of fasteners, such as friction fasteners, tape tabs or mechanical fasteners like hook-and-loop fasteners etc., may be used to fasten the articles to the underwear or around the waist of the user. Some absorbent articles are in the form of pants and therefore do not need special fastening means. In other cases, the absorbent article is worn in special elastic pants without the need for additional fasteners.

The absorbent structure can be of any conventional kind. Examples of commonly occurring absorbent materials are cellulosic fluff pulp, tissue layers, highly absorbent polymers (so called superabsorbents), absorbent foam materials, absorbent nonwoven materials or the like. It is common to combine cellulosic fluff pulp with superabsorbents in an absorbent structure. It is also common to have absorbent structures comprising layers of different material with different properties with respect to liquid acquisition capacity, liquid distribution capacity and storage capacity. This is well-known to the person skilled in the art and does therefore not need to be described in detail. The thin absorbent bodies, which are common in today's absorbent articles, often comprise a compressed mixed or layered structure of cellulosic fluff pulp and superabsorbent. The size and absorbent capacity of the absorbent structure may be varied to be suited for different uses, such as sanitary napkins, panty liners, adult incontinence pads and diapers, baby diapers, pant diapers, etc.

It is understood that the absorbent article described above and shown in the drawings only represents non-limiting examples and that the present invention is not limited thereto, but can be used in any type of absorbent articles as defined above.

All embodiments of a delivery device 1 as previously disclosed can be placed either on or in an absorbent article 50 as further explained below.

FIGS. 1-5 all show illustrative examples of absorbent articles 50 comprising a delivery device 1.

FIGS. 2*a-b*, 3*a-b* and 4*a-b* all show illustrative examples of delivery devices 1 being placed on the user facing side of the top sheet 55 of an absorbent article 50. In this (and the following) embodiment(s) of an absorbent article 50, the further advantage of the delivery device 1 of certain embodiments of the invention in that the third layer 25 of the delivery device 1 provides the possibility of attaching the delivery device 1 to an absorbent article 50, becomes apparent. Attachment may, e.g., be performed by ultrasonic welding, gluing, sewing or heat and/or cold sealing. Thereby, the delivery device 1 stays in place on the absorbent article 50 during transport, storage and use. Also, in this way, an esthetically attractive product is provided, wherein the delivery device is an integrated part of the absorbent product. The advantages of being able to attach the delivery device via the third layer have further been discussed above.

FIGS. 2*c-d*, 3*c-d* and 4*c-d* all show alternative variants of different embodiments of a delivery device 1, wherein the third layer 25 replaces the top sheet 55 and thereby also takes the role of a top sheet 55.

One further advantage with the embodiments, wherein the third layer 25 is the top sheet 55 of the absorbent article 50, is that the delivery device 1 can easily be positioned and attached to the absorbent article 50 to stay in place during transport, storage and use. Also, these embodiments have production advantages in that fewer production steps have to be performed when the top sheet 55 of the absorbent article 50 and the third layer 25 is the same layer. Also, the production of an absorbent article 50 according to this embodiment is cheaper as one material layer fulfills the functions both the top sheet 55 of the absorbent article 50 and the third layer 25. In addition, as the third layer 25 is the top sheet 55 of the absorbent article 50, when the deliver device 1 is attached to the absorbent article 50, the attachment may be performed distantly from the first layer 5 and second layer 10 of encapsulating material enclosing the additive 15. Thereby, the possible negative impact of the attachment method on the additive 15 is minimized.

Figure 5A:
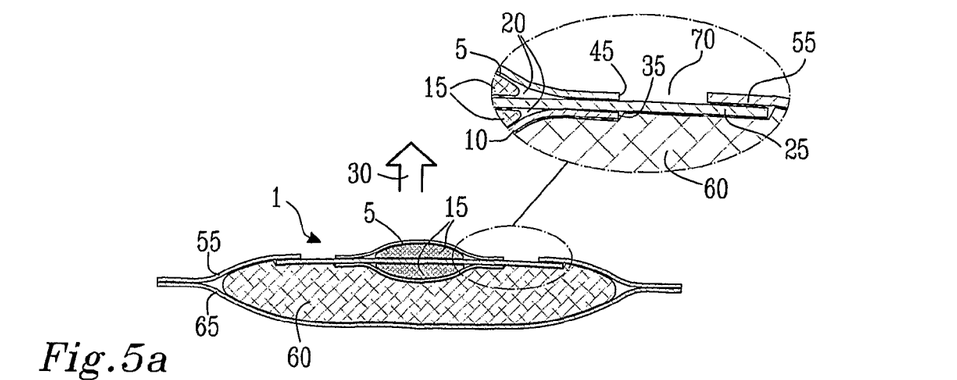
Figure 5B:
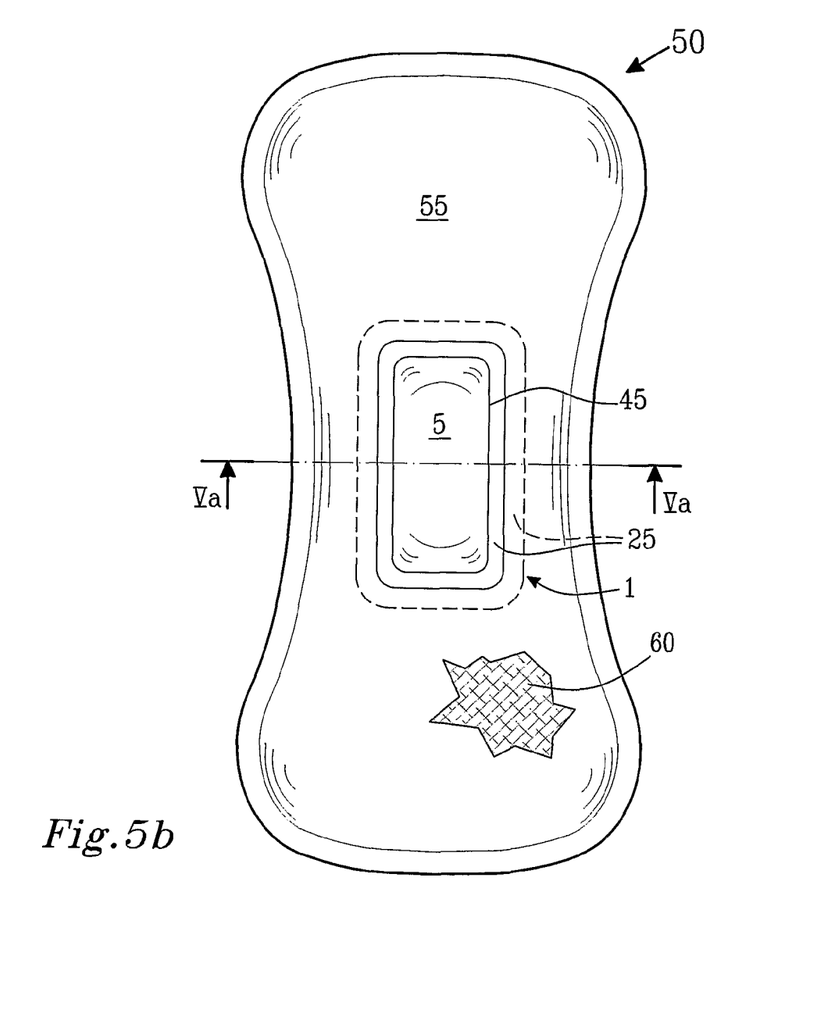

Alternatively, in another preferred embodiment of an absorbent article 50 comprising a delivery device 1, illustrated in FIG. 5, the delivery device 1 is inserted into an opening 70 cut out in the top sheet 55 of the absorbent article 50. In this embodiment, the third layer 25 acts as the top sheet in the central part of the absorbent article 50 where the delivery device 1 is placed. The third layer 25 may preferably be attached, e.g., by ultrasonic welding, gluing, sewing or heat and/or cold sealing, to the top sheet 55 of the absorbent article 50 on the lower side of the top sheet 55, i.e., the side of the top sheet 55 that faces the absorbent structure 60 of the absorbent article 50, to hold the delivery device 1 in place in the absorbent article 50 during transport, storage and use. The user facing side of the absorbent article 50 comprising the delivery device 1 is indicated by an arrow 30 pointing towards the user. FIG. 5 shows how a delivery device 1 wherein the third layer 25 extends throughout the delivery device 1, is placed in an opening in the top sheet 55 of an absorbent article 50. However, as the skilled person readily understands, other embodiments of delivery devices 1 disclosed herein, may also be placed in an absorbent article 50 in this way.

For the production of a delivery device 1, the third layer 25 may be in the form of a continuous web. This is an advantageous since current machines for producing absorbent articles are adapted to handle continuous webs of material. The delivery device 1 is formed on the continuous web by attaching the encapsulating material on each side of the continuous web, i.e., the third layer 25. This assembling may be made in a separate process step, independent of the high production speed of the above machines.

The delivery device 1 wherein the third layer 25 is in the form of a continuous web may either be assembled with the other component forming the absorbent article according to FIG. 2c-d, 3c-d and 4c-d by using standard techniques for laying down topsheets on absorbent articles, or to form an absorbent article according to FIGS. 2a-b, 3a-b, 4a-b and 5a-b by using the slip and cut process disclosed in EP 122846.

In another embodiment, not illustrated by a figure, the delivery device may be placed inside the absorbent structure 60 of an absorbent article 50. Importantly, in this embodiment, the first layer 5 and/or second layer 10 of encapsulating material should comprise a material that disintegrates during use of the absorbent article comprising the delivery device. Also in this embodiment, the third layer 25 has the advantage of providing a possibility to attach the delivery device to the absorbent article 50.

A further advantage with a delivery device 1 and absorbent article 50 disclosed herein, is that the additive 15, may be prevented from leaking out to the absorbent article 50, before or during use, and thereby impair the function of, e.g., the top sheet 55 of the absorbent article 50 and/or the absorbent structure 60.

A sanitary article may comprise at least one delivery device 1, such as one, two or three delivery devices. When an absorbent article 50 comprises more than one delivery device 1, these devices are preferably spaced apart in the longitudinal direction. Also, when the sanitary article comprises more than one delivery device 1, the different delivery devices 1 may comprise the same or different additives 15. One delivery device 1 may for instance comprise probiotic bacteria and another (an) odor inhibiting substance(s).

The invention claimed is:

1. A sanitary article comprising a delivery device for delivery of an additive, said delivery device comprising a first layer and a second layer of encapsulating material, said first layer being defined by first edges and said second layer being defined by second edges, said first layer being placed on a user facing side of the delivery device in relation to the second layer, said first layer and second layer of encapsulating material forming a space enclosing said additive, wherein the delivery device further comprises a third layer positioned on a user facing side of the second layer of encapsulating material, said third layer extending beyond and thereby covering at least substantially all of the second edges of the second layer of encapsulating material without covering all of the first layer of encapsulating material.

2. A sanitary article according to claim 1, wherein the third layer extends at least 1.5 mm outside of the edges of the second layer of encapsulating material.

3. A sanitary article according to claim 1, wherein the first layer and the second layer are sealed together along their edges.

4. A sanitary article according to claim 1, wherein the third layer is placed between the first layer and the second layer of encapsulating material.

5. A sanitary article according to claim 4, wherein the third layer extends substantially throughout the space formed between the first layer and the second layer of encapsulating material.

6. A sanitary article according to claim 1, wherein the third layer comprises a porous material.

7. A sanitary article according to claim 6, wherein said porous material comprises non-woven, wadding or filter foam.

8. A sanitary article according to claim 1, wherein the third layer comprises a plastic film.

9. A sanitary article according to claim 8, wherein the plastic film is perforated.

10. A sanitary article according to claim 1, wherein the first layer or the second layer of encapsulating material is water vapor impermeable.

11. A sanitary article according to claim 10, wherein the first layer or the second layer of encapsulating material comprises a metal foil.

12. A sanitary article according to claim 11, wherein said metal foil is aluminium foil.

13. A sanitary article according to claim 1, wherein the first layer or the second layer of encapsulating material comprises a polymeric film.

14. A sanitary article according to claim 13, wherein said polymeric film is selected from the group consisting of polyethylene, polypropylene, polyesters, polyvinylchloride, polyvinyldichloride, cyclic olefinic copolymers, copolymers and mixtures thereof, metallized polyolefins and plastic laminates with ceramic barrier.

15. A sanitary article according to claim 1, wherein the first layer or the second layer of encapsulating material comprises a laminate comprising a polymeric material.

16. A sanitary article according to claim 15, wherein said polymeric material is selected from the group consisting of polyethylene, polypropylene, polyesters, polyethylene terephtalate, polyvinylchloride, polyvinyldichloride, cyclic olefinic copolymers, polyolefins, metallized polyolefins, ethylene vinylacetate copolymer, ethylene ethyl acrylate copolymers, ethylene butyl acrylate copolymers, polyamides, polyvinyl alcohols, starch based polymers, poly lactic acid, ionomer, copolymers and mixtures thereof, and plastic laminates with ceramic barrier.

17. A sanitary article according to claim 1, wherein the additive comprises a skin caring agent.

18. A sanitary article according to claim 17, wherein the skin caring agent is an oil or a lotion.

19. A sanitary article according to claim 1, wherein the additive comprises a prebioticum, a pH regulating substance, a hydrophobic substance, an antibacterial substance, an antifungal substance, and/or an aromatic substance.

20. A sanitary article according to claim 1, wherein the additive comprises ZnO.

21. A sanitary article according to claim 1, wherein the additive is moisture sensitive.

22. A sanitary article according to claim 21, wherein said moisture sensitive additive comprises probiotic bacteria.

23. A sanitary article according to claim 22, wherein said probiotic bacteria are lactic acid producing bacteria.

24. A sanitary article according to claim 21, wherein said moisture sensitive additive comprises an odor inhibiting substance.

25. A sanitary article according to claim 24, wherein said odor inhibiting substance is zeolites and/or silica.

26. A sanitary article according to claim 1, wherein the additive further comprises a pharmaceutically acceptable carrier, excipient and/or diluent.

27. A sanitary article according to claim 26, wherein said pharmaceutically acceptable carrier is a hydrophobic carrier.

28. A sanitary article according to claim 1, wherein said first layer of encapsulating material is removed upon use of the delivery device to expose the additive.

29. A sanitary article according claim 1, wherein the sanitary article is a hygiene tissue.

30. A sanitary article according to claim 1, wherein the sanitary article is an absorbent article.

31. A sanitary article according to claim 30, wherein the delivery device is placed in an opening in said top sheet.

32. A sanitary article according to claim 30, wherein the third layer is said top sheet.

33. A sanitary article according to claim 30, wherein the absorbent article is a sanitary napkin, panty liner, sanitary panty or tampon; a diaper or a pant diaper for an infant or incontinent adult; an incontinence pad; or a diaper insert.

34. A sanitary article according to claim 1, comprising two or more delivery devices.

35. A sanitary article according to claim 1, wherein the second layer of encapsulating material extends beyond the edges of the first layer of encapsulating material in a direction substantially parallel to the user facing side of the delivery device.

36. A sanitary article according to claim 1, wherein the third layer is directly attached to the user facing side of the second layer of encapsulating material.

37. A sanitary article according to claim 1, wherein the third layer does not cover any of the first layer of encapsulating material.

38. A sanitary article comprising a delivery device for delivery of an additive, said delivery device comprising a first layer and a second layer of encapsulating material, said first layer being defined by first edges and said second layer being defined by second edges, said first layer being placed on a user facing side of the delivery device in relation to the second layer, said first layer and second layer of encapsulating material forming a space enclosing said additive, wherein the delivery device further comprises a third layer positioned on a user facing side of the second layer of encapsulating material, said third layer extending beyond and thereby covering at least substantially all of the second edges of the second layer of encapsulating material, wherein the absorbent article comprises a top sheet, said delivery device being placed on said top sheet.

* * * * *